| United States Patent [19] | [11] Patent Number: 4,913,906 |
| --- | --- |
| Friedman et al. | [45] Date of Patent: Apr. 3, 1990 |

[54] NOVEL CONTROLLED RELEASE DOSAGE FORM OF VALPROIC ACID

[76] Inventors: Michael Friedman, 11 Ejn Gedi Street; Meir Bialer, 36 Hachalutz Street; Avraham Rubinstein, 24 Nahage Hapredot St., all of Jerusalem; Upd Dufrovsky, 24 Yehuda Hanassi Street, Tel-Aviv, all of Israel

[21] Appl. No.: 832,244

[22] Filed: Feb. 24, 1986

[30] Foreign Application Priority Data

Feb. 28, 1985 [IL] Israel ........................................ 74468

[51] Int. Cl.$^4$ .............................................. A61K 9/50
[52] U.S. Cl. ..................... 424/499; 424/469; 424/480; 424/482
[58] Field of Search ............... 424/469, 480, 482, 486, 424/464, 468, 474, 475, 477, 478

[56] References Cited

U.S. PATENT DOCUMENTS

| 3,814,812 | 6/1974 | Eymard | 514/578 |
| 4,301,176 | 11/1981 | Grabowski et al. | 514/557 |
| 4,457,907 | 7/1984 | Porter | 424/482 |
| 4,606,909 | 8/1986 | Bechgaard et al. | 424/469 |
| 4,638,014 | 1/1987 | Clark | 514/619 |
| 4,699,927 | 10/1987 | Deboeck et al. | 514/564 |

*Primary Examiner*—Ellis P. Robinson
*Assistant Examiner*—Leon R. Horne
*Attorney, Agent, or Firm*—Browdy and Neimark

[57] ABSTRACT

The invention relates to controlled release pharmaceutical compositions. These contain as active ingredient valproic acid, a salt of valproic acid, an ester of valproic acid, Valpromide, or any other pharmaceutically acceptable derivative of valproic acid which upon administration to humans provides a serum level of valproic acid, in combination with an additive which is selected from physiologically acceptable polymeric substances and from native proteins. The active ingredient is usually in the range of from 10 to 80 weight percent. The novel pharmaceutical compositions are prepared by applying a high pressure to a mixture of the ingredients. They result in a prolonged serum level of the active ingredient.

12 Claims, 2 Drawing Sheets

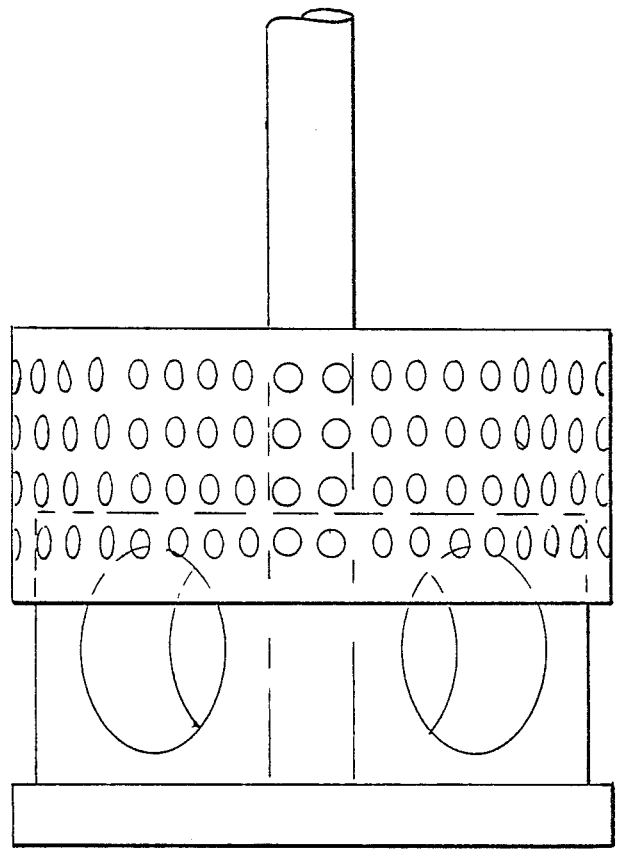
FIG 1 : Rotating basket used in dissolution studies of VPDCR ( Formulation 4 )

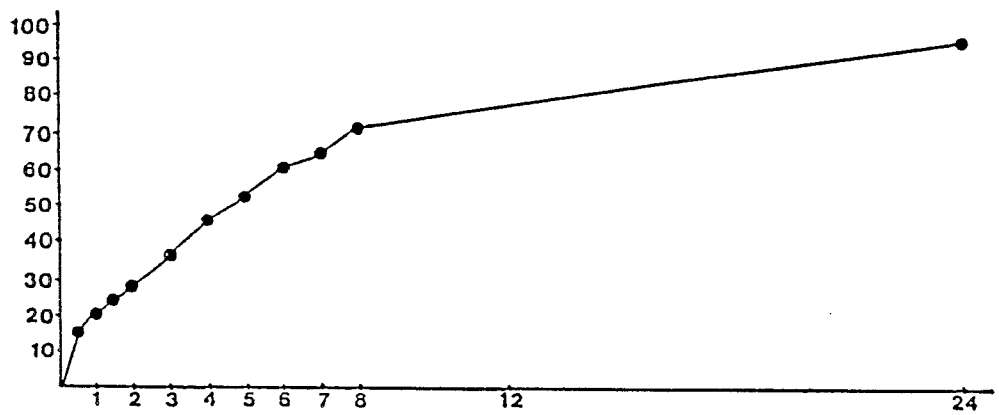
FIG. 2: TYPICAL DISSOLUTION RATE TEST OF VPDCR
(FORMULATION 4)
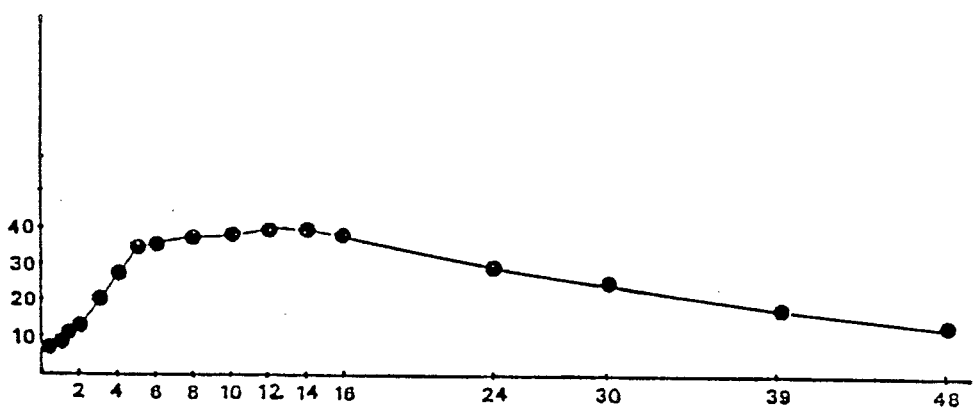
FIG. 3: VPA MEAN SERUM LEVELS IN 6 VOLUNTEERS AFTER ORAL
ADMINISTRATION OF VPDCR (FORMULATION 4)

NOVEL CONTROLLED RELEASE DOSAGE FORM OF VALPROIC ACID

FIELD OF THE INVENTION

The invention embraces novel controlled release dosage forms of a valproic acid (VPA), its sodium salt: sodium valproate (SVP), its primary amide: valpromide (VPD) and other derivatives of therapeutic value such as: 2-propylpentanol-di-n-propylactate, glycerol tri-dipropylacetate, divalproex sodium, etc.

The novel dosage forms are based on mixing the active ingredients with physiological and formulative compatible biodegradable or non-biodegradable polymers in an active ingredient/polymer ratio ranging between 10 to 80 percent w/w, then pressing the obtained mixture into tablets.

BACKGROUND OF THE INVENTION

Valproic acid (VPA) and its primary amide: Valpromide (VPD) are relatively new drugs that are now in common use: VPA, as an antiepileptic drug, and VPD as an antiepileptic and antipsychotic drug. VPA shows the shortest elimination half-life of all currently used antiepileptics. Its $t_{\frac{1}{2}}$ ranges between 6 to 17 hours in adults and 4 to 14 hours in children. This relatively short half-life of VPA is the reason for the frequently reported fluctuations in VPA plasma levels in chronic therapy. Such fluctuations are inconvenient in the management of epileptic patients and are a serious drawback in therapy.

Valpromide (VPO) is reported to biotransform to VPA before reaching the systemic circulation and therefore can be considered to be a VPA pro-drug. It also demonstrates slower absorption rate than valproic acid, resulting in fewer fluctuations in the drug plasma level, during chronic valpromide treatment.

A way of minimizing the oscillations in VPA plasma levels is by administering the drug in a sustained-release formulation.

Despite the many marketed VPA formulations, no satisfactory sustained-release dosage form of VPA exists at present. There exists a report about a once-a-day treatment of epilepsy with a sodium valproate enteric-coated tablet: A. Covanis and P. M. Jeavons, Dev. Med. Child Neurol., 22, 202 (1980). The benefit of a VPA sustained release dosage form of a VPA-prodrug is well realized as it decreases the dosage regimen of the drug in chronic therapy.

SUMMARY OF THE INVENTION

Orally administered controlled release dosage forms of valproic acid (VPA), its sodium salt: sodium valproate (SVP), its primary amide: valpromide (VPD), and other derivatives of therapeutic value such as 2-propylpentanol-di-n-propylacetate, glycerol tri-dipropylacetate and di sodium valproate are provided. The control release dosage forms of the drugs are based on a predetermined gradual release of the active ingredients in the biological fluids, resulting in a sustained action of the valproic acid with but small fluctuations of the plasma level over prolonged periods of time.

According to the invention there are provided dosage forms of valproic acid (VPA), its esters, salts or its primary amide, thereof, in combination with a predetermined quantity of an additive which is physiologically acceptable and which results in the desired gradual and sustained release of the drug. The preferred additives are: derivatives of cellulose such as carboxymethylcellulose, ethylcellulose, methylcellulose, hydroxypropyl cellulose, polyvinyl alcohol, polyethylene, polypropylene, polystyrene, polyacrylamide, ethylene vinyl acetate copolymer, polyacrylate, polyurethane, polyvinylpyrrolidone, polymethylmethacrylate, polyvinyl acetate, polyhydroxyethyl methacrylate, and waxes such as paraffin. Especially advantageous results were attained with hydroxypropyl cellulose. There may also be used combinations of these, or a combination with a native protein. Sustained release formulations of valpromide were prepared with native proteins, such as soy protein, collagen, gelatine, ovalbumine, milk albumin, casein, etc. Especially advantageous results were obtained with soy protein.

The active ingredient generally comprises from about 10 to 80 percent w/w of the unit dosage form, the preferred range being between 20 to about 60 percent w/w of the unit dosage form. The dosage forms are intended for oral administration. They generally comprise from 100 to about 500 mg of the active drug, the total weight of the tablet being from about 500 to 1000 mg. An appreciable serum level is attained after about 2 hours from the time of administration, and this gradually increases. The therapeutic serum level of VPA is kept for at least 12 hours after administration and after 24 hours, there still exists a substantial serum level, as will become apparent hereinafter.

The controlled release dosage forms are prepared by first forming an intimate mixture of the active substance with the additive, preferably in a dry atmosphere, when sodium valproate is used and pressing tablets at a force of from about 2000 to 5000 kg/cm$^2$. With VPD it is advantageous to prepare an intimate mixture of the drug and the additive, granulate the mixture with some water, drying, milling the granulate, sieving and forming tablets under an adequate pressure, and if desired, sterilizing under UV.

BRIEF DESCRIPTION OF THE DRAWINGS

FIG. 1 is a rotating basket used in dissolution studies.

FIG. 2 illustrates a typical dissolution rate test of VPDCR.

FIG. 3 illustrates VPA mean serum levels in 6 volunteers after administration of VPDCR.

The invention is illustrated hereinafter with reference to a number of examples of specific nature. There are intended to exemplify the invention, and these are not to be construed in a limiting manner. It is clear that other polymeric substances, such as other cellulose derivatives can be used instead. It is also clear that soy protein is by way of example only and that other suitable additives, such as other suitable native proteins or mixtures of these, can be used with satisfactory results.

EXAMPLE:

Sodium valproate controlled releas (VPACR) tablets based on Hydroxy Propyl Cellulose

| | Ingredient | mg/tablet |
|---|---|---|
| Formulation 1: | Sodium Valproate | 200.0 |
| | Hydroxy Propyl Cellulose* | 600.0 |
| Formulation 2: | Sodium Valproate | 333.3 |
| | Hydroxy Propyl Cellulose* | 666.6 |
| Formulation 3: | Sodium Valproate | 500.0 |

-continued

| Ingredient | mg/tablet |
|---|---|
| Hydroxy Propyl Cellulose | 500.0 |

*Klucel, H.F., Hercules BV, Holland

EXAMPLE:

Sodium Valproate controlled relase (VPACR) tablets based on Ethyl Cellulose

| | Ingredient | mg/tablet |
|---|---|---|
| Formulation 4: | Sodium Valproate | 200.0 |
| | Ethyl Cellulose** | 600.0 |
| Formulation 5: | Sodium Valproate | 200.0 |
| | Ethyl Cellulose** | 400.0 |
| Formulation 6: | Sodium Valproate | 100.0 |
| | Ethyl Cellulose** | 500.0 |

**Type N-100, Assia, Israel

EXAMPLE:

Sodium Valproate controlled release (VPACR) tablets based on esters of acrylic and methacrylic acid***

| | Ingredient | mg/tablet |
|---|---|---|
| Formulation 7: | Sodium Valproate | 200.0 |
| | Eudragit RS | 600.0 |
| Formulation 8: | Sodium Valproate | 100.0 |
| | Eudragit RS | 500.0 |

***Eudragit RS, Rohm Pharma, W. Germany

EXAMPLE:

Valpromide controlled release (VPDCR) tablets based on Soy Protein

| | Ingredient | mg/tablet |
|---|---|---|
| Formulation 9: | Valpromide | 300.0 |
| | ARDEX-D Dispersable**** | 300.0 |
| Formulation 10: | Valpromide | 300.0 |
| | ARDEX-R**** | 300.0 |
| Formulation 11: | Valpromide | 300.0 |
| | ARDEX-F | 300.0 |
| Formulation 12: | Valpromide | 300.0 |
| | ARDEX-DHV**** | 300.0 |

****Manufactured by Archer Daniels Midland Company, U.S.A.

EXAMPLE:

Mode of preparation of VPACR tablets
(a) Mixing of the ingredients in the correct proportions until a homogeneous mixture is obtained.
(b) Pressing the mixture under 5000 kg force to obtain plain tablets.

When formulating sodium valproate it is recommended to process the abovementioned preparation in a dry atmosphere cabinet (less than 30% R.H.).

EXAMPLE:

Mode of preparation of VPDCR tablets
(a) Mixing of the ingredients in the correct proportions until a homogeneous mixture is obtained.
(b) Granulating the mixture with the aid of purified water.
(c) Drying the mixture for 1 hr at 60° C. in a well ventilated shelves oven.
(d) Milling the granulate in an oscilator equipped with a 20 mesh screen.
(e) Pressing the obtained granulate under 3000 kg force to obtain 600 mg plain tablets.
(f) Irradiation of the obtained tablets under u.v. light (254 nm) for 3 minutes.

DISSOLUTION RATE STUDIES

Tables 1-4 represent typical results from dissolution rate tests of VPACR and VPDCR formulations.

VPACR formulations were tested according to the U.S.P. XX method described on p. 959 and in the following media and durations: 3 hours in pH=2 buffer* and additional 21 hours in pH=6.8 buffer** (total time 24 hours). The dissolution rate test systems were sampled in consistent intervals and volumes were adjusted respectively to 400 ml.

VPDCR formulations were tested in rotating basket FIG. 2 in simulated gastric and intestinal fluids U.S.P. XX, 37° C., as follows: 1 hour in gastric juice and additional 23 hours in intestinal fluid. The systems were sampled in consistent intervals and volumes were adjusted respectively to 1000 ml.

PHARMACOKINETIC ANALYSIS

After orally administering VPACR formulations 1-3, to six healthy volunteers (in separate cross-over clinical studies) a prolonged absorption of VPA had been achieved, resulting in a sustained duration of VPA serum levels within the therapeutic window (50-100 1 mcg.ml) up till 24 hours with bioequivalence to

| *Buffer pH = 2: | KCl | 0.2 N | 25.0% | w/v |
|---|---|---|---|---|
| | HCl | 0.2 N | 5.3% | w/v |
| | Purified water to | | | 100.0% |
| **Buffer pH = 6.8 | KH$_2$PO$_4$ | 0.2 M | 25.0% | w/v |
| | NaOH | 0.2 N | 11.83% | w/v |
| | Purified water to 100.0% | | | | commercial formulation (Depakine-Labaz) (Table 5), (M. Bialer, M. Friedman, J. Dubrovsky, I. Raz and O. Abramsky, in press in Biopharm. Drug Dispos. (1985)).

After orally administering VPACR formulation to six healthy volunteers (in separate cross-over clinical study) a prolonged absorption of VPA had been achieved, resulting in a sustained duration of VPA serum levels reaching the lower limit of the therapeutic window (Table 6). A theoretical calculation of once daily multiple treatment, assuming constant dose of 900.0 mg and 24 hours interval yield satisfactory results considering VPDCR as a once a day controlled release dosage form (A. Rubinstein, M. Friedman, M. Bialer, I. Raz and O. Abramsky, submitted to J. Controlled Release (1985)).

Examples of Derivatives of Valproic Acid of Therapeutic Value:

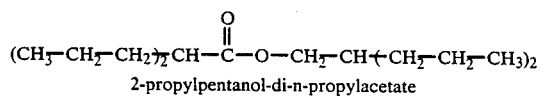

2-propylpentanol-di-n-propylacetate

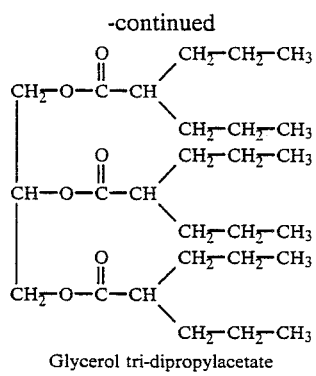

Glycerol tri-dipropylacetate

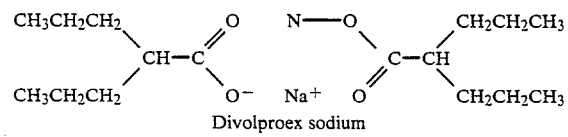

Divolproex sodium

TABLE 1

Typical dissolution rate profiles of valproic acid controlled. release formulations based on Hydroxy Propyl Cellulose

| Time (h) | % released | | |
|---|---|---|---|
| | Formulation 1 | Formulation 2 | Formulation 3 |
| 0.5 | | 12 | 17.6 |
| 1 | 15 | 16.5 | 23.5 |
| 2 | 21 | 22.5 | 34 |
| 3 | 23 | 27.6 | 40 |
| 4 | 31 | 39.3 | 59 |
| 5 | 37 | 47.4 | 64 |
| 6 | 45 | 54.3 | 71.6 |
| 7 | 49 | 60.0 | 81 |
| 8 | 57.5 | 65.7 | 83 |

Key:
Formulation 1: Each tablet contains Sodium valproate 200.0 mg Klucel HF 600.0 mg
Formulation 2: Each tablet contains: Sodium valproate 333.3 mg Klucel HF 666.6 mg
Formulation 3: Each tablet contains: Sodium Valproate 500.0 mg Klucel HF Klucel HF 500.0 mg

TABLE 2

Typical dissolution rate profiles of valproic acid controlled release formulations based on Ethyl Cellulose (formulations 4–6)

| Time (h) | % Released | | |
|---|---|---|---|
| | Formulation 4 | Formulation 5 | Formulation 6 |
| 1 | 28 | 35 | 28 |
| 2 | 39 | 51 | 36 |
| 3 | 44 | 66 | 50 |
| 4 | 60 | 78 | 70 |
| 5 | 67 | 80 | 79 |
| 6 | 83 | 81 | |
| 7 | 75 | 85 | 83 |
| 8 | 76 | 85 | 87 |
| 9 | 77 | 85 | 88 |
| 10 | 78 | — | 89 |
| 11 | 80 | — | 91 |
| 12 | 82 | — | 93 |
| 24 | 84 | — | 94 |

Key:
Formulation 4: Each tablet contains: Sodium Valproate 200.0 mg Ethyl Cellulose 600.0 mg
Formulation 5: Each tablet contains: Sodium Valproate 200.0 mg Ethyl Cellulose 400.0 mg
Formulation 6: Each tablet contains: Sodium Valproate 100.0 mg Ethyl Cellulose 500.0 mg

TABLE 3

Typical dissolution rate profiles of valproic acid controlled release formulations based on Eudragit RS (formulations 7, 8)

| Time (h) | % RELEASED | |
|---|---|---|
| | Formulation 7 | Formulation 8 |
| 1 | 32 | 32 |
| 2 | 60 | 57 |
| 3 | 73 | 66 |
| 4 | 79 | 73 |
| 5 | 80 | 74 |
| 6 | 82 | 75 |
| 7 | 84 | 79 |
| 8 | 85 | 80 |
| 9 | — | 81 |
| 10 | — | — |

Key:
Formulation 7: Each tablet contains: Sodium Valproate 200.0 mg Eudragit RS 600.0 mg
Formulation 8: Each tablet contains: Sodium Valproate 100.0 mg Eudragit RS 500.0 mg

TABLE 4

Typical dissolution rate profiles of valpromide controlled release formulations based on several ARDEX types (formulations 9–12)

| Time (h) | % Released | | | |
|---|---|---|---|---|
| | Formulation 9 | Formulation 10 | Formulation 11 | Formulation 12 |
| 0.5 | 18.1 | 4.0 | 4.0 | 4.0 |
| 1 | 20.5 | 6.0 | 7.0 | 6.5 |
| 1.5 | 24.7 | 8.0 | 8.5 | 8.0 |
| 2 | 28.45 | 9.5 | 10.5 | 9.5 |
| 3 | 37.0 | 12.5 | 14.0 | 13.0 |
| 4 | 46.0 | 17.5 | 19.5 | 16.0 |
| 5 | 52.6 | 20.0 | 23.5 | 21.5 |
| 6 | 61.2 | 23.0 | 26.5 | 25.5 |
| 7 | 64.8 | 24.0 | 31.5 | 28.0 |
| 8 | 80.0 | 26.0 | 39.9 | 28.5 |
| 12 | | 37.5 | 45.5 | 42.0 |
| 24 | 97.0 | 59.0 | 63.5 | 73.0 |

Key:
Formulation 9: Each tablet contains: Valpromide 300.0 mg ARDEX D-Dispersible 300.0 mg
Formulation 10: Each tablet contains: Valpromide 300.0 mg ARDEX R 300.0 mg
Formulation 11: Each tablet contains: Valpromide 300.0 mg ARDEX F 300.0 mg
Formulation 12: Each tablet contains: Valpromide 300.0 mg ARDEX DHV 300.0 mg

TABLE 5

Mean VPA serum concentration of formulations 1–3 after oral administration to six volunteers

| Time (h) | VPA serum concentration mg/ml:mean ± S.D. | | |
|---|---|---|---|
| | Formulation 1 | Formulation 2 | Formulation 3 |
| 0.5 | 14.0 ± 4.7 | 15.5 ± 3.2 | 17.7 ± 8.0 |
| 1 | 16.3 ± 3.4 | 19.9 ± 3.8 | 28.7 ± 8.0 |
| 2 | 23.1 ± 5.9 | 30.2 ± 8.3 | 39.1 ± 5.1 |
| 3 | 30.8 ± 7.6 | 44.01 ± 11.6 | 45.8 ± 3.6 |
| 4 | 38.9 ± 5.9 | 54.1 ± 11.7 | 54.4 ± 6.8 |
| 5 | 44.7 ± 6.6 | 54.7 ± 9.8 | 56.4 ± 5.7 |
| 6 | 50.2 ± 6.1 | 58.6 ± 10.9 | 58.7 ± 6.8 |
| 8 | 54.8 ± 5.7 | 60.0 ± 8.6 | 60.6 ± 7.5 |
| 10 | 59.3 ± 10.0 | 66.4 ± 9.2 | 64.2 ± 7.6 |
| 12 | 59.3 ± 14.6 | 65.0 ± 10.2 | 63.6 ± 7.5 |
| 14 | 55.3 ± 15.2 | 64.2 ± 11.2 | 62.2 ± 5.2 |
| 16 | 52.3 ± 16.6 | 56.7 ± 5.4 | 64.4 ± 10.4 |
| 24 | 41.1 ± 15.7 | 45.0 ± 10.1 | 51.8 ± 12.0 |
| 30 | 30.1 ± 11.6 | 32.4 ± 8.8 | 38.7 ± 10.4 |
| 39 | 21.6 ± 10.6 | 20.5 ± 7.0 | 25.3 ± 6.2 |
| 48 | 13.9 ± 7.1 | 13.8 ± 5.2 | 15.6 ± 5.4 |

TABLE 6

Mean VPA serum concentration of VPDCR-formuation 9, after oral administration to six volunteers

| Time | VPA serum concentration (mcg/ml ± S.D.) |
|---|---|
| 0.5 | 7.94 ± 3.92 |

TABLE 6-continued

Mean VPA serum concentration of VPDCR-formuation 9, after oral administration to six volunteers

| Time | VPA serum concentration (mcg/ml ± S.D.) |
|---|---|
| 1 | 8.85 ± 4.36 |
| 1.5 | 11.47 ± 4.2 |
| 2 | 13.27 ± 3.84 |
| 3 | 20.8 ± 6.78 |
| 4 | 27.8 ± 11.22 |
| 5 | 34.58 ± 16.5 |
| 6 | 35.75 ± 15.23 |
| 8 | 37.6 ± 12.08 |
| 10 | 38.45 ± 9.33 |
| 12 | 39.6 ± 6.99 |
| 14 | 40.0 ± 9.23 |
| 16 | 38.9 ± 10.25 |
| 24 | 29.8 ± 13.4 |
| 30 | 25.34 ± 10.3 |
| 39 | 18.47 ± 7.1 |
| 48 | 14.7 ± 5.85 |

The combination of the active substance and the additives used according to the invention results in the unexpected result of an oral dosage form whereby a biologically active level can be maintained for a period of 24 hours.

I claim:

1. A controlled release oral dosage form comprising an essentially homogenous admixture of an active ingredient selected from the group consisting of, pharmaceutically acceptable salts and esters of valproic acid, valpromide (VPD), and other VPA derivatives which biotransform to provide VPA in human serum, and a physiologically acceptable polymer said active ingredient comprising from about 10 to about 80 weight percent of said dosage form in an amount effective to provide a prolonged serum level of VPA.

2. A dosage form according to claim 1 wherein the polymer is at least one member selected from the group consisting of carboxymethyl cellulose, methyl cellulose, ethylcellulose, hydroxypropyl cellulose, polyvinyl alcohol, polyethylene, polypropylene, polystyrene, polyacrylamide, ethylene vinyl acetate copolymer, polyacrylate, polyurethane, polyvinylpyrrolidone, polymethylmethacrylate, polyvinyl acetate, polyhydroxyethyl methacrylate, and waxes.

3. A dosage form according to claim 1, wherein the active ingredient is VPD and the polymer is a native protein selected from the group consisting of soy protein, collagen, gelatin, ovalbumine, milk albumin, casein and mixtures thereof.

4. A dosage form according to claim 1, wherein the tablet contains fromm 200 to 500 mg of the active ingredient.

5. A process for preparing oral dosage forms for the sustained release of valproic acid esters, salts thereof, or VPD, which comprises producing an essentially homogenous admixture of an active ingredient selected from the group consisting of valproic acid, pharmaceutically acceptable salts and esters of VPA, valpromide (VPD), and other VPA derivatives which biotransform to provide VPA in human serum, and a physiologically acceptable polymer in an amount effective to provide a prolonged serum level of VPA, and forming tablets of said admixture under high pressure.

6. A process according to claim 5, where the pressure is 1000 to 5000 kg/cm$^2$.

7. The dosage form of claim 4, containing at least 300 mg of said polymer.

8. The process of claim 5, wherein said active ingredient is sodium valproate, and said process is performed in a dry atmosphere cabinet at less than 30% R.H.

9. The dosage form of claim 1, wherein said polymer is soy protein.

10. The dosage form of claim 9, comprising about equal weights of soy protein and valpromide.

11. The dosage form of claim 10, wherein said weight of said valpromide is about 300 mg.

12. A tablet according to claim 7.

* * * * *

REEXAMINATION CERTIFICATE (4097th)

United States Patent [19]
Friedman et al.

[11] B1 4,913,906
[45] Certificate Issued Jun. 6, 2000

[54] CONTROLLED RELEASE DOSAGE FORM OF VALPROIC ACID

[75] Inventors: Michael Friedman; Meir Bialer; Avraham Rubinstein, all of Jerusalem; Upd Dufrovsky, Tel-Aviv, all of Israel

[73] Assignee: Yissum Research Development Company of the Hebrew University of Jerusalem, Jerusalem, Israel

Reexamination Request:
No. 90/005,413, Jul. 3, 1999

Reexamination Certificate for:
Patent No.: 4,913,906
Issued: Apr. 3, 1990
Appl. No.: 06/832,244
Filed: Feb. 24, 1986

[30] Foreign Application Priority Data

Feb. 28, 1985 [IL] Israel .......................................... 74468

[51] Int. Cl.$^7$ ..................................................... A61K 9/50
[52] U.S. Cl. .......................... 424/499; 424/469; 424/480; 424/482
[58] Field of Search .................................... 424/499, 469, 424/480, 482

[56] References Cited

PUBLICATIONS

Bailer, M., *Animal Models in the Primary Screening of Controlled Release Formulations.* 183–193, no date avail.

Bailer, M., *Comparative Pharmacokinetic Analysis of a Novel Sustained Release Dosage Form of Valproic Acid in Dogs*, Biopharmaceutics & Drug Disposition, vol. 5, 1–10 (1984).

Bailer, M., *Development and Pharmacokinetic Evaluation of Novel Sustained–Release Dosage Forms of Valproic Acid in Humans and Dogs*, Labo–Pharma–Probl., Tech 32, No. 341, Apr. 1984.

Bailer, M., *Effect of Sustained Release in the Pharmacokinetics of Valproic Acid in the Dog*, Int'l. J. of Pharm., 20(1984).

Bailer, M., *Pharmacokinetic Evaluation of Novel Sustained–Release Dosage Forms of Valproic Acid in Humans*, Biopharmaceutics & Drug Disposition, vol. 6, 401–411 (1985).

Bailer, M., *Pharmacokinetic Evaluation of Novel Sustained–Release Dosage Form of Valproic Acid and Intravenous Preparation of Valpromide in Dogs*, Metabolism of Antiepileptic Drugs, Raven Press (1984).

Bailer, M., *Pharmacokinetic Ealuation of Sustained Release Formulations of Antiepileptic Drugs*, Clin. Pharmacokinet., 22(1) 11–21, 1992.

Bailer, M., *Relation Between Absorption Half–Life Values of Four Novel Sustained–Release Dosage Forms of Valproic Acid in Dogs and Humans*, Biopharmaceutics & Drug Disposition, vol. 7, 495–500 (1986).

*Primary Examiner*—Thurman K. Page

[57] ABSTRACT

The invention relates to controlled release pharmaceutical compositions. These contain as active ingredient valproic acid, a salt of valproic acid, an ester of valproic acid, Valpromide, or any other pharmaceutically acceptable derivative of valproic acid which upon administration to humans provides a serum level of valproic acid, in combination with an additive which is selected from physiologically acceptable polymeric substances and from native proteins. The active ingredient is usually in the range of from 10 to 80 weight percent. The novel pharmaceutical compositions are prepared by applying a high pressure to a mixture of the ingredients. They result in a prolonged serum level of the active ingredient.

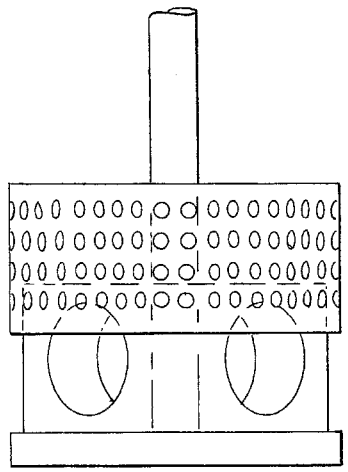

: Rotating basket used in dissolution studies of VPDCR ( Formulation 4 )

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–12 is confirmed.

\* \* \* \* \*